United States Patent [19]

Steffen

[11] Patent Number: 4,693,996

[45] Date of Patent: Sep. 15, 1987

[54] METHOD OF TREATING HEART FAILURE AND MEDICAMENTS THEREFOR

[75] Inventor: Robert P. Steffen, Saline, Mich.

[73] Assignee: Warner-Lambert Company, Morris Plains, N.J.

[21] Appl. No.: 812,876

[22] Filed: Dec. 23, 1985

[51] Int. Cl.$^4$ .............................................. A61K 31/70
[52] U.S. Cl. .................................... 514/46; 514/252; 536/26
[58] Field of Search ...................... 514/46, 252; 536/26

[56] References Cited

U.S. PATENT DOCUMENTS

| | | | |
|---|---|---|---|
| 3,471,472 | 10/1969 | Thiel et al. | 536/26 |
| 3,838,147 | 9/1974 | Pohlke et al. | 536/26 |
| 4,353,905 | 10/1982 | Sircar et al. | 514/252 |
| 4,501,735 | 2/1985 | Trivedi et al. | 514/46 |

FOREIGN PATENT DOCUMENTS

| | | | |
|---|---|---|---|
| 0049658 | 4/1982 | European Pat. Off. | 514/252 |
| 0051020 | 5/1982 | European Pat. Off. | 514/252 |
| 0069846 | 5/1982 | European Pat. Off. | 514/252 |

*Primary Examiner*—Johnnie R. Brown
*Attorney, Agent, or Firm*—Joan Thierstein

[57] ABSTRACT

The present invention relates to a combination of selected cardiotonic agents with selected adenosine receptor agonist antihypertensive agents resulting in a synergistic increase in myocardial contractility and cardiac output thereby rendering such combinations useful in treating heart failure.

5 Claims, 2 Drawing Figures

METHOD OF TREATING HEART FAILURE AND MEDICAMENTS THEREFOR

BACKGROUND OF THE INVENTION

Cardiotonic agents such as substituted 4,5-dihydro-6-[4-(1H-imidazol-1-yl)phenyl]-3(2H)-pyridazinones and 6-[4-(1H-imidazol-1-yl)phenyl]-3(2H)-pyridazinones are described in U.S. Pat. No. 4,353,905.

Antihypertensive agents which have been found to possess differing affinities at adenosine receptors are $N^6$-(1- and 2-benzocycloalkyl)adenosines described in U.S. Pat. No. 4,501,735.

Combinations of the above noted cardiotonic agents and selected antihypertensive agents which attribute their activity to inhibition of angiotensin-converting enzyme (ACE inhibitors) are described in U.S. Ser. No. 612,275 filed May 21, 1984, now U.S. Pat. No. 4,584,299. Other combinations of antihypertensive agents and diuretics are well-known in the art. ACE-inhibiting antihypertensive agents have also been reported to be useful in combination with diuretics, saluretics, α-adrenolytic, β-blockers, calcium antagonists or vascular dopaminergic receptor agonists. See European Patent Publications 51,020, 69,846, and 49,658.

The present invention relates to a combination of selected cardiotonic agents with selected adenosine receptor agonist antihypertensive agents resulting in a synergistic increase in myocardial contractility and cardiac output thereby rendering such combinations useful in treating heart failure.

SUMMARY OF THE INVENTION

Accordingly the present invention relates to a pharmaceutical composition for increasing cardiac contractility and cardiac output comprising:

(a) an effective amount of a compound of the formula

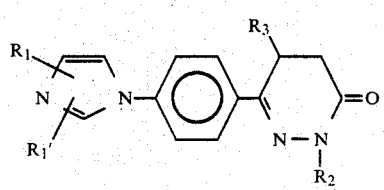

I wherein $R_1$ and $R_1'$ are independently hydrogen or alkyl of one to three carbon atoms; $R_2$ is hydrogen, alkyl of one to three carbon atoms or 2-hydroxyethyl; and $R_3$ is hydrogen or alkyl of one to three carbon atoms, or a pharmaceutically acceptable acid addition salt thereof, with (b) an effective amount of a compound of the formula

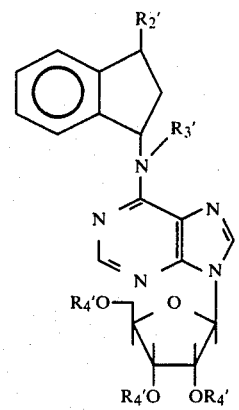

II wherein $R_2'$ and $R_3'$ are independently hydrogen or alkyl of one to three carbon atoms; and $R_1'$ is hydrogen, acetyl or benzoyl, its diastereomers or mixtures thereof, or a pharmaceutically acceptable acid addition salt thereof, and a pharmaceutically acceptable carrier.

The present invention also relates to a method of treating heart failure in a subject suffering therefrom comprising administering to said subject a combination of (a) an effective amount of a compound of the formula I or a pharmaceutically acceptable acid addition salt thereof with (b) an effective amount of a compound of the formula II, its diastereomers or mixtures thereof, or a corresponding pharmaceutically acceptable acid addition salt thereof, and a pharmaceutically acceptable carrier.

BRIEF DESCRIPTION OF THE DRAWING

The drawing consists of FIG. 1 and FIG. 2.

DETAILED DESCRIPTION

Figure 1:
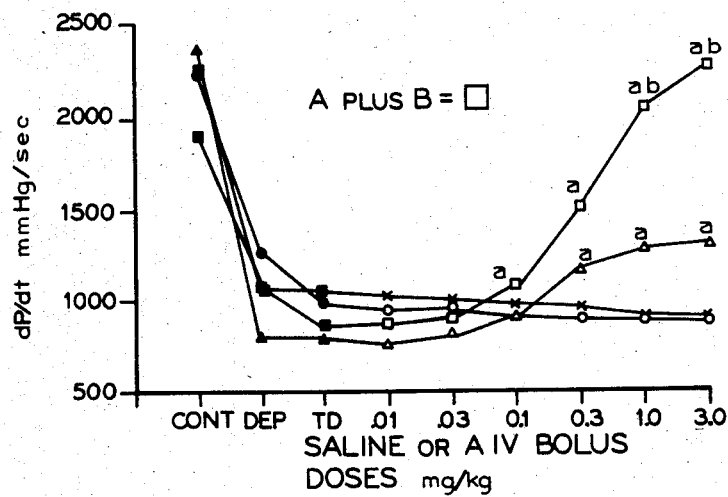
FIG. 1 shows the effect of saline and the hydrochloride salt of 4,5-(dihydro-6-[4-(1H-imidazol-1-yl)phenyl]-3(2H)pyridazinone (A) in 6 animals (n=6) as Δ; saline and saline, n=6, as x; (R)-N-(2,3-dihydro-1H-inden-1-yl) adenosine (B) and the hydrochloride salt of 4,5-(dihydro-6-[4-(1H-imidazol-1-yl)phenyl]-3(2H)-pyridazinone, (A) n=6, as □; (R)-N-(2,3-dihydro-1H-inden-1-yl)adenosine (B) and saline, n=6, as 0; on left ventricular contractility (dP/dt) plotted as milimeters of mercury/second (mmHg/sec) on the vertical axis against intravenous (IV) bolus doses (mg/kg) on the transverse axis and on cardiac output (CO) plotted as liters/min (l/min) on the vertical axis against the intravenous (IV) bolus doses (mg/kg) on the transverse axis. CONT indicates the control before propanolol induced cardiac depression, DEP indicates a stable propanolol depression, and TD indicates administration of the initial test drug, either saline or (R)-N-(2,3-dihydro-1H-inden-1-yl)adenosine (B). The closed figures represent the administration of the initial test drug component of the indicated combination and, the open figures represent the hydrochloride salt of 4,5-(dihydro-6-[4-(1H-imidazol-1-yl)phenyl]-3(2H-pyridazinone (A) or saline administration with the respective intial test drug to provide the combination defined for each symbol defined above. "a" indicates significant difference (p<0.05) from TD based on intragroup comparison. "b" indicates significant difference (p<0.05) from saline and the hydrochloride salt of 4,5-(dihydro-6-[4-(1H-imidazol-1-yl)phenyl]-3(2H)-pyridazinone (A).
Figure 1A:
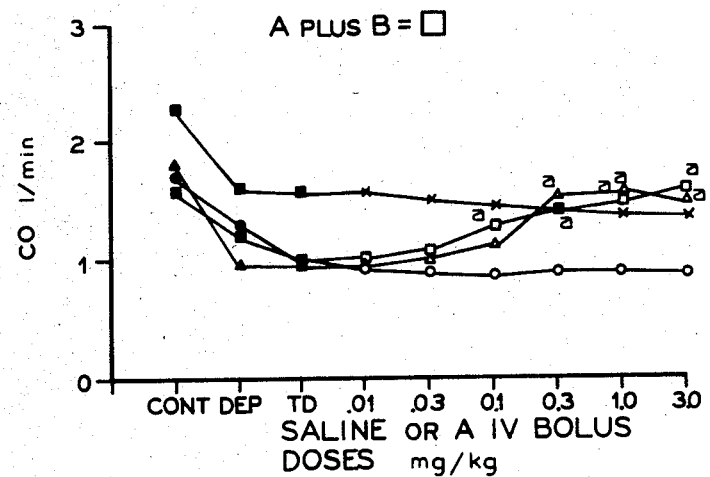

The compounds of formula I have been reported as cardiotonic agents and their effectiveness demonstrated in standard pharmacological test procedures, for example, in causing a significant increase in myocardial contractility in the pentobarbital anesthetized dog with low or minimal changes in heart rate and blood pressure, see U.S. Pat. No. 4,353,905 and U.S. application Ser. No. 515,799 filed July 22, 1983 and U.S. application Ser. No. 612,275 filed May 21, 1984. Also see U.S. Pat. No. 4,551,455.

The compounds of formula II have been reported to possess differing affinities at adenosine receptors having highly desirable cardiovascular activities, such as antihypertensive and antianginal. The antihypertensive activity indicates use for the treatment of high blood pressure. Increases in coronary blood flow indicate utility for the treatment of angina and myocardial ischemia. See U.S. Pat. No. 4,501,735.

This invention relates to the discovery that the combination of a cardiotonic agent as defined above with an adenosine receptor agonist as defined above results in a synergistic increase in myocardial contractility and cardiac output and therefore may be used in pharmaceutical compositions for treating heart failure.

Preferred combinations are those containing (a) a compound of formula I wherein $R_1$, $R_1'$, and $R_2$ are hydrogen, and $R_3$ is hydrogen or methyl, with (b) a compound of formula II wherein $R_2'$ and $R_3'$ are hydrogen or methyl and $R_4'$ is hydrogen.

Particular preferred combinations in pharmaceutical composition form are those containing the hydrochloride salt of 4,5-dihydro-6-[4-(1H-imidazol-1-yl)-phenyl]-3(2H)pyridazinone as the cardiotonic agent and (R)-N-(2,3-dihydro-1H-inden-1-yl) adenosine as the adenosine receptor agonist.

The adenosine receptor agonists in the combination have asymmetric carbon atoms. The compounds accordingly exist as optical isomers and diastereomers as racemates and mixtures thereof. All of these are within the scope of the invention. The compound of formula I used in this invention has the R configuration at the $N^6$ position. This configuration has been shown to be required for biological activity, and thus the adenosine receptor agonists of the invention are derived from either R or RS-(2,3-dihydro-1H-inden-1-yl) amine or lower alkyl amine.

The cardiotonic compounds of formula I can be produced as described in U.S. Pat. No. 4,353,905. The antihypertensive adenosine receptor agonists can be produced as described in U.S. Pat. No. 4,501,735.

According to this invention, a combination of a cardiotonic compound and an antihypertensive adenosine receptor agonist is administered in an effective amount which comprises a total daily dosage of about 0.1 to 200 mg, preferably 1 to 20 mg of cardiotonic agent and about 1 mg to 500 mg and preferably from 5 to 100 mg of the adenosine receptor agonist to a subject, e.g., a mammalian species, including human, suffering from heart failure. Such total daily dosages can be used in a single administration of the total amount or in divided doses two to four times daily. Generally once or twice daily is preferred. This preferred dosage is about 3 to 60 mg of cardiotonic agent and 0.3 to 6 mg of the antihypertensive adenosine receptor agonist once daily or about 1 to 20 mg of cardiotonic and about 0.1 to 2 mg of adenosine receptor agonist twice daily. The preferred route of administration is oral.

The pharmaceutical compositions of the invention can take any of a wide variety of oral and parenteral dosage forms. The dosage forms comprise as the active components, a cardiotonic compound as defined previously and an adenosine receptor agonist as defined previously as free bases and free acids thereof or as corresponding pharmaceutically acceptable salts.

For preparing pharmaceutical compositions, one uses inert, pharmaceutically acceptable carriers that can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compounds. In the tablet, the active compounds are mixed with carrier having the necessary binding properties in suitable proportions and compacted in the shape and size desired. The powders and tablets preferably contain from 5% or 10% to about 70% of active ingredients. Suitable solid carriers are magnesium carbonate, magnesium stearate, talc, sugar, lactose, pectin, dextrin, starch, gelatin, tragacanth, methyl cellulose, sodium carboxymethyl cellulos, a low melting wax, cocoa butter, and the like. The term "preparation" is intended to include the formulation of the active compounds with encapsulating materials as carrier, providing a capsule in which the active components (with or without other carriers) are surrounded by carrier, which are thus in association with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active components in water with viscous material, i.e., natural or synthetic gums, resins, methyl cellulose, sodium carboxymethyl cellulose, and other well-known suspending agents.

Preferably, the pharmaceutical preparation is in unit dosage form. In such form, the preparation is subdivided into unit doses containing appropriate quantities of active components. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compounds in a unit dose of preparation may be varied or adjusted from 1 mg to 200 mg according to the particular application and the potency of the active ingredients.

In therapeutic use as a cardiotonic agent, the compositions are constituted such that the active ingredients content can be conveniently at the initial oral dosage of about 0.03 mg to about 10 mg per kilogram of weight. An active ingredients content such as to give a dose range of about 0.1 mg to about 3 mg of active ingredients per kilogram is preferred.

The pharmaceutical compositions preferably are constituted so that they can be administered parenterally or orally. Solutions of the active compounds as free bases and free acids or pharmaceutically acceptable salts can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, paragens, chlorobutanol, phenol, sorbic acid, thimerosal, and the like. In many cases, it will be preferable to include isotonic agents, for example, sugars or sodium chloride. Prolonged absorption of the injectable compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients, into a sterile vehicle which contains the basic dispersion medium and the required other ingredients from those enumerated above. In the case of the sterile powders for the preparation of sterile injectable solutions, the preferred methods of preparation are vacuum drying and the freeze-drying technique which yield a powder of active ingredients plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well-known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suitable as unitary dosages for the mammalian subjects to be treated; each unit containing a predetermined quantity of active materials calculated to produce the desired therapeutic effect in association with the required pharmaceutical carrier. The specification for the novel dosage unit forms of the invention are dictated by and directly dependent on (a) the unique characteristics of the active materials and the particular therapeutic effect to be achieved, and (b) the limitation inherent in the art of compounding such active materials for the treatment of disease in living subjects having a diseased condition in which bodily health is impaired as herein disclosed in detail.

The principal active ingredients are compounded for convenient and effective administration in effective amounts with a suitable pharmaceutically acceptable carrier in dosage unit form as hereinbefore disclosed. A unit parenteral dosage form can, for example, contain the principal active compounds in amounts ranging from about 0.03 to about 100 mg, with from about 0.1 to 50 mg being preferred. Expressed in proportions, the active compounds are generally present in from about 0.03 to about 100 mg/ml of carrier. The daily parenteral doses for mammalian subjects to be treated ranges from 0.03 mg/kg to 30 mg/kg. The preferred daily dosage range is 0.3 mg/kg to 10 mg/kg.

The active substances described above form commonly known, pharmaceutically acceptable salts such as alkali metal and other common basic salts or acid addition salts, etc. References to the base substances are therefore intended to include those common salts known to be substantially equivalent to the parent compound and described in the above referenced patents.

The following nonlimiting examples illustrate the inventors' preferred methods for preparing the compounds of the invention.

EXAMPLE 1

4,5-dihydro-6-[4-(1$\underline{H}$-imidazol-1-yl)phenyl]-3(2$\underline{H}$)-pyridazinone A solution of 4.5 g of 4-(1$\underline{H}$-imidazol-1-yl)-$\gamma$-oxobenzenebutanoic acid in ethanol (60 ml) is heated under reflux with 85% hydrazine hydrate (2.5 ml) for 17 hours. The alcohol is evaporated off, the residue is treated with water and filtered. The crude product is finally crystallized from ethanol to yield 3.5 g of the product 4,5-dihydro-6-[4-(1$\underline{H}$-imidazol-1-yl)phenyl]-3(2$\underline{H}$)-pyridazinone: mp. 206°–207° C. (dec.).

Anal. Calcd. for $C_{13}H_{12}N_4O$: C=65.00; H=5.00; N=23.33; Found: C=65.06; H=5.35; N=23.39.

Hydrochloric acid-addition salt of 4,5-dihydro-6-[4-(1$\underline{H}$-imidazol-1-yl)phenyl]-3(2$\underline{H}$)-pyridazinone is prepared by adding an ethanolic solution of hydrochloric acid to a hot solution of about 70 g of 4,5-dihydro-6-[4-(1H-imidazol-1-yl)phenyl]-3(2H)-pyridazinone in about 1400 ml of ethanol to a pH of about 2.0, chilling the mixture and collecting the precipitated salt.

EXAMPLE 2

N(6)-[1-(R)-indanyl]adenosine

For 20 hours, 1.83 g 6-chloropurine riboside, 0.95 g (R) (-)-1-aminoindane and 0.862 g triethylamine are refluxed in 50 ml absolute ethanol under nitrogen atmosphere. The solvent is evaporated to dryness and residue is treated with 50 ml cold water. The solid material is filtered, dissolved in excess ethanol, and volatiles are evaporated under reduced pressure to remove water. Residue upon treatment with ethanol affords solid material. It is filtered and dried. One more crop of the same material is obtained from the mother liquor yielding 1.46 g (60% of theory) of N(6) [1-(R)-indanyl]adenosine having a melting point of 185°-187° C.

Anal. Calcd. for $C_{19}H_{21}N_5O_4$: C=59.52; H=5.52; N=18.26; Found: C=59.00; H=5.50; N=18.05.

The following representative Examples 3 through 6, are given as illustrative pharmaceutical compositions utilizing different carriers. In these examples, Example 3 illustrates the use of the combination of compounds of the invention in injectables suitable for intravenous or other types of injection into the host subject. Example 4 is directed to an oral syrup preparation, Example 5 to an oral capsule preparation, and Example 6 to oral tablets. In each of Examples 3 through 6, the ingredients are first listed and are then followed by the method of preparing the composition.

EXAMPLE 3

INJECTABLES 4,5-dihydro-6-[4-(1H-imidazol-1-yl)-phenyl]-3 (2H)-pyridazinone, hydrochloride salt (A) 10 mg–200 mg.

(R)-N-(2,3-dihydro-1H-inden-1-yl)adenosine (B) 1 mg–100 mg.

Water for Injection USP q.s.

The hydrochloride salt of product (A) and product (B) are dissolved in water and passed through a 0.22 micron filter. Aliquots of the filtered solution is added to ampoules or vials, sealed and sterilized.

EXAMPLE 4

SYRUP

| 200 mg Active ingredients/5 ml syrup | |
|---|---|
| COMPOUND A (EXAMPLE 3) | 12.5 g |
| COMPOUND B (EXAMPLE 3) | 1.25 g |
| Purified Water USP | 200 ml |
| Cherry Syrup q.s. or | 1000 ml |

Compounds A and B are dissolved in the water and to this solution the syrup is added with mild stirring.

EXAMPLE 5

CAPSULES

| 50 mg, 100 mg or 200 mg | |
|---|---|
| COMPOUND A (EXAMPLE 3) | 250 g |
| COMPOUND B (EXAMPLE 3) | 25 g |
| Lactose USP. Anhydrous q.s. or | 250 g |

| -continued | |
|---|---|
| 50 mg, 100 mg or 200 mg | |
| Sterotex Powder HM | 5 g |

Combine COMPOUNDS A, B, and the Lactose in a Tumble blend for two minutes, blend for one minute with the intensifier bar and then tumble blend again for one minute. A portion of the blend is then mixed with the Sterotex Powder, passed through a #30 screen and added back to the remainder of the blend. The mixed ingredients are then blended for one minute, blended with the intensifier bar for thirty seconds and tumble blended for an additional minute. Appropriate sized capsules are filled with 141 mg, 352.5 mg or 705 mg of the blend, respectively, for the 50 mg, 125 mg, and 250 mg containing capsules.

EXAMPLE 6

TABLETS

| 50 mg, 100 mg or 200 mg | |
|---|---|
| COMPOUND A (EXAMPLE 3) | 125 g |
| COMPOUND B (EXAMPLE 3) | 12.5 g |
| Corn Starch NF | 200.0 g |
| Cellulose, Microcrystalline | 46.0 g |
| Sterotex Powder HM | 4.0 g |
| Purified Water q.s. or | 300.0 ml |

Combine the corn starch, the cellulose and COMPOUNDS A and B, together in a planetary mixer and mix for two minutes. Add the water to this combination and mix for one minute. The resulting mix is spread on trays and dried in a hot air oven at 50° C. until a moisture level of 1 to 2 percent is obtained. The dried mix is then milled with a Fitzmill through a #RH2B screen, and added back to the milled mixture and the total blended for five minutes by drum rolling. Compressed tablets of 150 mg, 375 mg, and 750 mg, respectively, of the total mix are formed with appropriate sized punches for the 50 mg, 125 mg, or 500 mg containing tablets.

The usefulness of the pharmaceutical compositions of the present invention as cardiotonic preparations is demonstrated by the synergy of the combined active components contained therein in standard pharmacological test procedures. The following is illustrative:

I. Adenosine Receptor Agonist Activity of (R)-N-(2,3-dihydro-1H-inden-1-yl)adenosine (B).

In generally known methods using isolated rat brain membranes to assay $A_1$ and $A_2$ adenosine receptor binding it is found that (R)-N-(2,3-dihydro-1H-inden-1-yl)adenosine (B) has $IC_{50}$ values for $A_1$ and $A_2$ of 0.03 and 0.81M, respectively. However, it is also found that (R)-N-(2,3-dihydro-1H-inden-1-yl)adenosine (B) does not significantly bind dopaminergic, muscarinic, $\alpha_1$ and $\alpha_2$-adrenergic, $\beta_1$ and $\beta_2$-adrenergic, serotonergic, or $\alpha$-aminobuteric acid receptors.

Concentration-dependent increases in coronary flow and decreases in heart rate produced by (R)-N-(2,3-dihydro-1H-inden-1-yl)adenosine (B) is shown in isolated-Langendorff perfused rat hearts by a method substantially as described in using $10^{-8}-3\times10^{-6}$M of (R)-N-(2,3-dihydro-1H-inden-1-yl)adenosine.

In a procedure essentially as described in the above noted U.S. Pat. No. 4,501,735, (R)-N-(2,3-dihydro-1H-inden-1-yl)adenosine (B) produces dose-related decreases in mean arterial blood pressure and heart rate. In this procedure the (R)-N-(2,3-dihydro-1H-inden-1-yl)adenosine (B) is administered intravenously (IV) at 3 to 300 mg/kg in anesthetized-vagotomized normotensive rats.

Finally, dose-related decreases in mean arterial blood pressure, heart rate, and calculated total peripheral resistance are produced by (R)-N-(2,3-dihydro-1H-inden-1-yl)adenosine (B) by administration intravenously (IV) to anesthetized normotensive dogs. Such administration is by a method essentially described as follows:

Mongrel dogs of either sex are anesthetized with sodium pentobarbital (30 mg/kg IV) and mechanically ventilated with room air. The left and right femoral veins are cannulated for injection of test compound and maintenance anesthesia (3.5 mg/kg/hr), respectively. Cardiac output is measured by a thermodilution catheter positioned in the pulmonary artery. Left ventricular contractility (dP/dt) is measured by a Millar Mikro-Tip catheter pressure transducer positioned in the left ventricular cavity via the left carotid artery, heart rate, and lead II electrocardiogram are recorded continuously. Each animal is allowed 30 minutes to stabilize and hemodynamic control pressures, cardiac output, and electrocardiographic measurements are recorded. Compounds are dissolved in saline if possible and pH adjusted. If another solvent is required, vehicle control experiments are performed. Test compounds are administered as rising bolus doses usually starting at 0.1 midtherapeutic and increasing in half log doses to 30 X midtherapeutic. All cardiovascular measurements are repeated after each dose.

Agent induced effects on any of the cardiovascular measurements are recorded.

II. Synergistic Hemodynamic Effect of the Adenosine Receptor Agonist, (R)-N-(2,3-dihydro-1H-inden-1-yl)adenosine (B), and the Cardiotonic, 4,5-dihydro-6-[4-(1H-imidazol-1-yl)phenyl]-3(2H)pyridazinone, hydrochloride salt (A) in Acute Heart Failure in the Anesthetized Dog.

Methods

Adult mongrel dogs of either sex are anesthetized with sodium pentobarbital (32 mg/kg) IV, trachea intubated, and ventilated artificially. Anesthesia is maintained by a continuous infusion of sodium pentobarbital (3.0 mg/kg/hr) through a femoral vein cannula. Three additional venous cannulae are used for (1) propranolol infusion, (2) (R)-N-(2,3-dihydro-1H-inden-1-yl)adenosine or saline infusion and (3) bolus injections of either 4,5-dihydro-6-[4-(1H-imidazol-1-yl)phenyl]-3(2H)pyridazinone, hydrochloride salt or saline. Systemic arterial blood pressure, left ventricular contractility (dP/dt), and heart rate are recorded continuously. Cardiac output, measured by thermodilution, is recorded before myocardial depression, when stable myocardial depression is achieved (approximately 30 minutes), and ten minutes following each bolus dose. Following surgical preparation, 30 minutes are allowed for hemodynamic stabilization prior to induction of the myocardial depression. Myocardial depression is induced and maintained by administration of dl-propranolol at 4 mg/kg IV bolus and continuous infusion at 0.125 mg/kg/min. Once stable depression is achieved (30-40 minutes), animals receive: (1) (R)-N-(2,3-dihydro-1H-inden-1-yl)adenosine at 6 µg/kg/min for 45 minutes followed by increasing IV bolus doses of 4,5-dihydro-6-[4-(1H-imidazol-1-yl)phenyl]-3(2H)pyradazinone, hydrochloride salt at 0.01 to 3.0 mg/kg, n=6 (number of animals) (R)-N-(2,3-dihydro-1H-inden-1-yl)adenosine/4,5-dihydro-6-[4-(1H-imidazol-1-yl)-3(2H)-pyridazinone, hydrochloride salt, (2) (R)-N-(2,3-dihydro-1H-inden-1-yl)adenosine followed by IV bolus doses of saline, n=6 ((R)-N-(2,3-dihydro-1H-inden-1-yl)adenosine/saline), (3) saline infusion followed by IV bolus doses of 4,5-dihydro-6-[4-(1H-imidazol-1-yl)phenyl]-3(2H)pyridazinone, hydrochloride salt at 0.01 to 3.0 mg/kg, n=6 (saline/4,5-dihydro-6-[4-(1H-imidazol-1-yl)phenyl]-3(2H)pyridazinone, hydrochloride salt), and (4) saline infusion followed by IV bolus doses of saline, n=6 (saline/saline). Intra- and inter-group comparisons are made using Duncan's Multiple Range test comparing doses to depression levels and dose to dose of 4,5-dihydro-6-[4-(1H-imidazol-1-yl)phenyl]-3(2H)pyridazinone, hydrochloride salt, respectively.

Results 4,5-dihydro-6-[4-(1H-imidazol-1-yl)phenyl]-3(2H)-pyridazinone, hydrochloride salt, (A) in the presence of (R)-N-(2,3-dihydro-1H-inden-1-yl)adenosine (B) produces greater increases in myocardial contractility (dP/dt of left ventricular pressure) and cardiac output than 4,5-dihydro-6-[4-(1H-imidazol-1-yl)phenyl]-3-(2H)pyridazinone, hydrochloride salt, (A) alone at comparable doses (FIG. 1).

Figure 2:
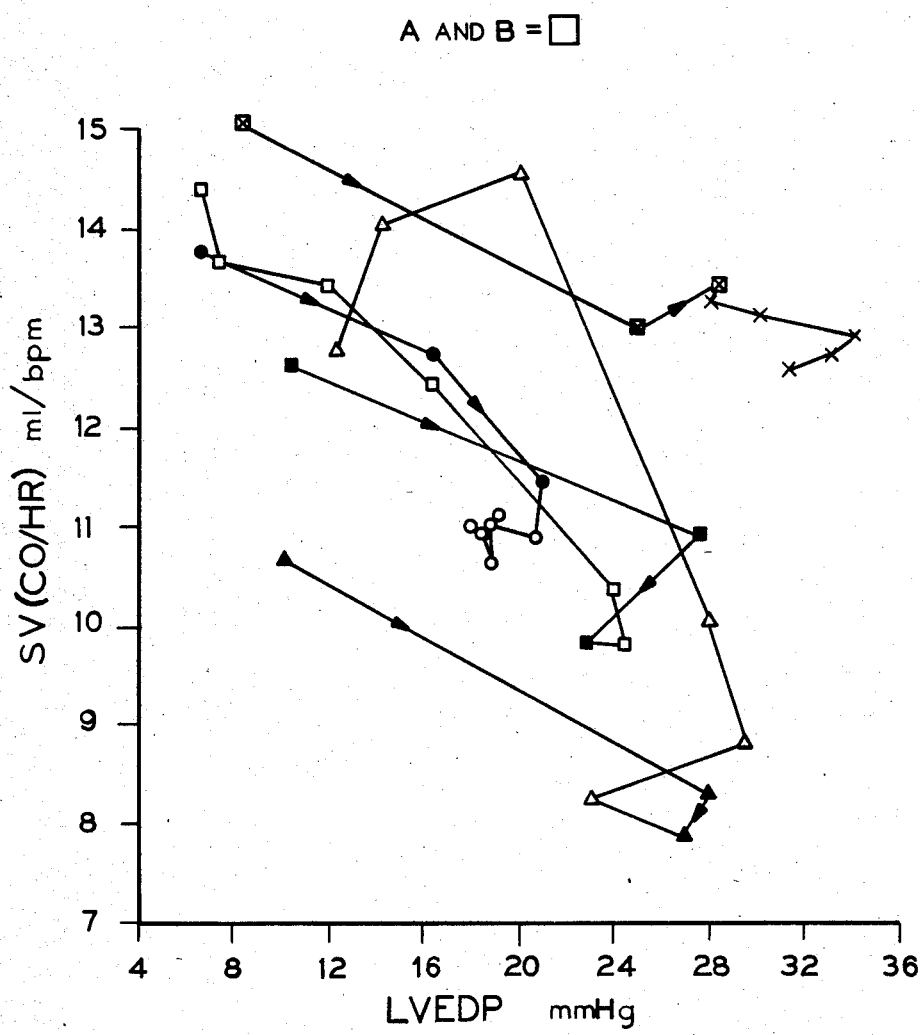
FIG. 2 shows the effect of saline and the hydrochloride salt of 4,5-(dihydro-6-[4-(1H-imidazol-1-yl)- phenyl]-3(2H)-pyridazinone (A) in 6 animals (n=6) as Δ; saline and saline, n=6, as x; (R)-N-(2,3-dihydro-1H-inden-1-yl) adenosine (B) and the hydrochloride salt of 4,5-(dihydro-6-[4-(1H-imidazol-1-yl)phenyl]-3(2H)-pyridazinone (A), n=6, as □; (R)-N-(2,3-dihydro-1H-inden-1-yl) adenosine (B) and saline, n=6, as 0; on left ventricular end diastolic pressure (LVEDP) on the transverse axis in mmHg plotted against stroke volume (SV) on the vertical axis. SV was calculated from CO and heart rate as cardiac output (CO)/heart rate (HR) or ml/bpm (mililiters/blood pressure). Further, in FIG. 2 the closed figures represent preadministration of the hydrochloride salt of 4,5-(dihydro-6-[4-(1H-imidazol-1-yl)phenyl]-3(2H)-pyridazinone (A) or saline and the open figures represent the dose period for the hydrochloride salt of 4,5-(dihydro-6-[4-(1H-imidazol-1-yl)phenyl]-3(2H)-pyridazinone (A) or saline in the combinations as indicated by each symbol.

FIG. 2 illustrates the effect of treatments on left ventricular pressure volume relationships. This figure shows that the combination of (R)-N-(2,3-dihydro-1Hinden-1-yl)adenosine (B) and 4,5-dihydro-6-[4-(1H-imidazol-1-yl)phenyl]-3-(2H)pyridazinone, hydrochloride salt, (A) produces a proportional left-upward shift of the pressure volume relationship of the left ventricle reflecting the improved hemodynamic performance observed with the combination of agents.

In view of the observation that (R)-N-(2,3-dihydro-1H-inden-1-yl)adenosine (B) per se did not increase dP/dt, cardiac output, or affect the pressure volume relationship, the results of this study indicate a synergistic and beneficial effect of the combination of (R)-N-(2,3-dihydro-1H-inden-1-yl)adenosine (B) and 4,5-dihydro-6-[4-(1H-imidazol-1-yl)phenyl]-3(2H)-pyridazinone, hydrochloride salt, (A) in a model of heart failure.

I claim:

1. A pharmaceutical composition for increasing myocardial contractility and cardiac output comprising
   (a) an effective amount of a compound of the formula

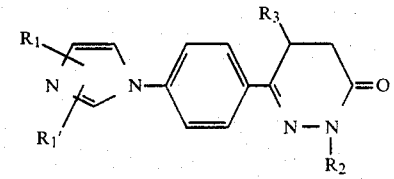

wherein $R_1$ and $R_1'$ are independently hydrogen or alkyl of one to three carbon atoms; $R_2$ is hydrogen, alkyl of one to three carbon atoms or 2-hydroxyethyl; and $R_3$ is hydrogen or alkyl of one to three carbon atoms, or a pharmaceutically acceptable acid addition salt thereof, with (b) an effective amount of a compound of the formula

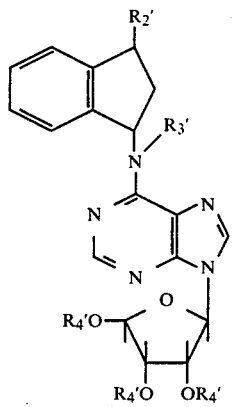

wherein $R_2'$ and $R_3'$ are independently hydrogen or alkyl of one to three carbon atoms; and $R_4'$ is hydrogen, acetyl or benzoyl; its diastereomers or mixtures thereof, or a pharmaceutically acceptable acid addition salt thereof, and a pharmaceutically acceptable carrier.

2. A composition according to claim 1 wherein in (a) $R_1$, $R_1'$ and $R_2$ are hydrogen and $R_3$ is hydrogen or methyl.

3. A composition as claimed in claim 2 wherein in (b), $R_2'$ and $R_3'$ are hydrogen or methyl and $R_4'$ is hydrogen.

4. A composition as claimed in claim 3 wherein in (a) the compound of formula I is the hydrochloride salt of 4,5-dihydro-6-[4-(1H-imidazol-1-yl)phenyl]-3(2H)-pyridazinone and in (b) the compound of formula II is (R)-N-(2,3-dihydro-1H-inden-1-yl) adenosine.

5. A method of treating heart failure in a subject suffering therefrom comprising administering to said subject a pharmaceutical composition as claimed in claim 1 in unit dosage form.

* * * * *